Figure 1:
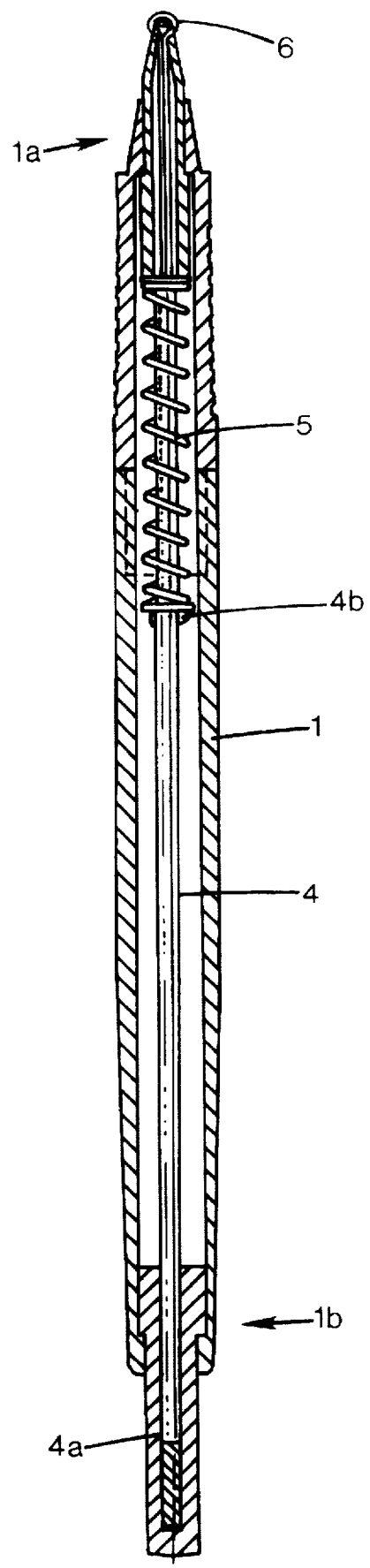

United States Patent [19]

Laxvik

[11] Patent Number: 5,792,148
[45] Date of Patent: Aug. 11, 1998

[54] DEVICE AND METHOD FOR REMOVAL OF TICKS FROM HUMANS AND ANIMALS

[76] Inventor: Lars Laxvik, Fridhem/Opphem, 590 41 Rimforsa, Sweden

[21] Appl. No.: 894,600

[22] PCT Filed: Mar. 12, 1996

[86] PCT No.: PCT/SE96/00316

§ 371 Date: Aug. 6, 1997

§ 102(e) Date: Aug. 6, 1997

[87] PCT Pub. No.: WO96/28102

PCT Pub. Date: Sep. 19, 1996

[30] Foreign Application Priority Data

Mar. 15, 1995 [SE] Sweden ............... 9500942

[51] Int. Cl.$^6$ ............... A61B 17/24; A61B 17/50
[52] U.S. Cl. ............... 606/131; 606/113
[58] Field of Search ............... 606/1, 110, 113, 606/114, 127, 128, 131, 205–211

[56] References Cited

U.S. PATENT DOCUMENTS

| | | | |
|---|---|---|---|
| 668,647 | 2/1901 | Jaenicke | 606/113 |
| 798,839 | 9/1905 | Stowe | 606/113 |
| 2,856,933 | 10/1958 | Hildebrand et al. | 606/113 |
| 4,538,611 | 9/1985 | Kelman | 606/113 |
| 4,938,764 | 7/1990 | Glaberson . | |
| 5,002,323 | 3/1991 | Idsund | 606/210 |
| 5,407,243 | 4/1995 | Riemann . | |

FOREIGN PATENT DOCUMENTS

| | | |
|---|---|---|
| 378166 A | 6/1985 | Austria . |
| 0027704 A2 | 4/1981 | European Pat. Off. . |
| 239112 A | 12/1945 | Switzerland . |

*Primary Examiner*—Glenn K. Dawson
*Attorney, Agent, or Firm*—Fasth Law Firm; Rolf Fasth

[57] ABSTRACT

The invention concerns a method and device for removing ticks from humans and animals. The device comprises: a base part (1) with at least one opening (2a, 2b), a thread loop (6) of resilient material which is arranged to be drawn into the opening (2a, 2b) under the effect of a spring member (5). The cross section of this opening relative to the thread loop (6) is such that the loop (6) outside the opening (2a, 2b), whilst being drawn thereinto, gradually decreases in size. Operatively connected to the thread loop (6) is a member (4, 4a) arranged such that, against the effect of the spring member (5), it shoots the thread loop (6) out of the opening (2a, 2b). According to the method of the invention, owing to pressure being exerted on the pushbutton (4a), the loop (6) is ejected from the opening (2a, 2b), laid around the tick and, since pressure is no longer exerted on the pushbutton (4a), can be drawn into the opening (2a, 2b). The loop (6) is then rotated one turn and the tick releases its grip within approximately three seconds.

3 Claims, 2 Drawing Sheets

DEVICE AND METHOD FOR REMOVAL OF TICKS FROM HUMANS AND ANIMALS

The present invention concerns a device for removing ticks from humans and animals.

The invention also concerns a method for removing ticks from humans and animals using this device.

Known arrangements of the above-mentioned type are tweezer-like instruments. However these instruments are difficult to use since considerable experience is required to use the instrument correctly without injuring the tick. Such injury to or pressure on the tick can give rise to tick-borne infections.

An object of the present invention is to provide of the initially mentioned type by means of which a tick can be removed rapidly and reliably so eliminating the above-mentioned disadvantaged. This object is achieved according to the invention in that the device comprises: a base part provided with two openings and a tip tapering at the openings; a thread of resilient material which passes through the openings and thus forms a loop outside the base part, the loop being arranged such that, under the effect of a helical spring disposed inside the base part, it is drawn in towards the openings, the loop outside the openings, under the drawing-in affect of the thread, gradually decreasing in size, and the spring being arranged to actuate the thread with such a force that a tick is not injured by the loop; and a rod of which one end is connected to the thread and of which the other end projects out of the base part at the opposite end to the tip and thus forms a pushbutton for discharging the thread loop against the effect of the spring.

The loop is preferably made of nylon thread as emerges from a particular feature of the invention.

A method of removing ticks from humans and animals using the device according to the invention is characterized in that, by exerting pressure on the pushbutton, the loop is ejected from the opening and is laid around the tick and in that, when pressure is no longer exerted on the pushbutton the loop can be drawn into the opening, whereupon the loop is rotated one turn and the tick releases its grip within approximately three seconds.

Figure 2:
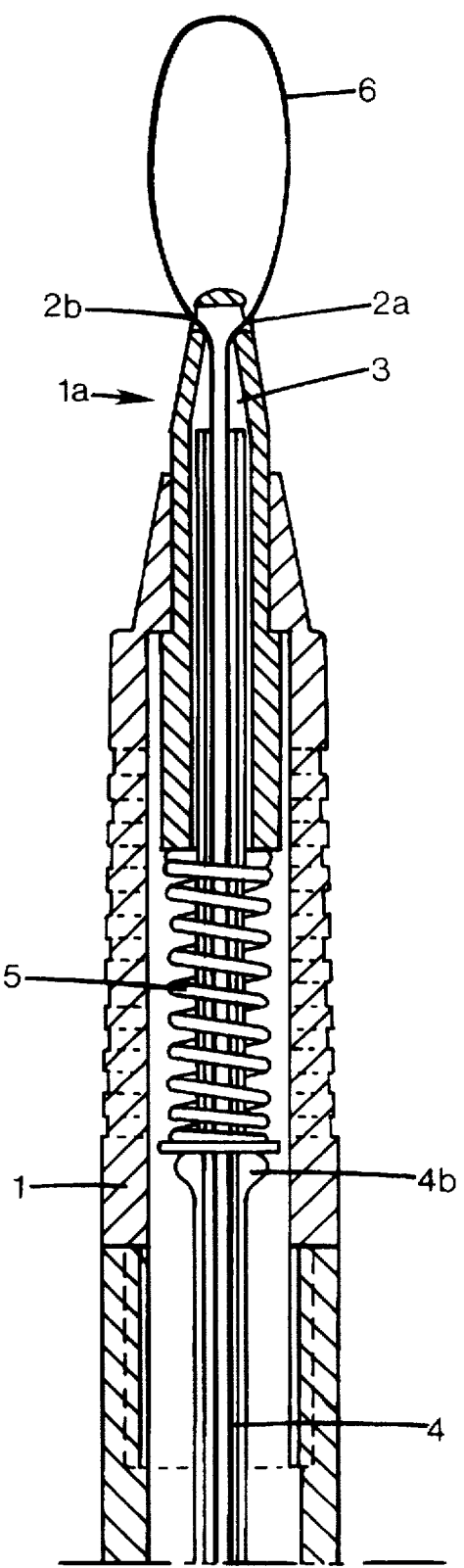

An embodiment of the device according to the invention is shown schematically in the enclosed drawing and will be explained in further detail in the following with reference to this drawing, in which:

FIG. 1 shows schematically and in longitudinal section an embodiment of the device; and FIG. 2 shows a detail view of FIG. 1, which shows clearly the loop before use.

In the drawings 1 designates a penholder-like base part which at its one conically tapering end 1a has two openings 2a, 2b which are widened to form a duct 3 inside the base part 1. Displaceably mounted in the duct 3 is a rod 4 which at the other end 1b of the base part 1 projects out the latter and forms a pushbutton 4a. When pressure is exerted on the pushbutton 4a a helical spring 5, which is tensioned between a spring stop 4b on the rod 4 and the base of the conically tapering part 1a of the base part 1 counteracts this movement.

Attached to the rod 4 at its end opposite the pushbutton 4a is a loop 6 of resilient material, for example, a nylon thread, which loop can be ejected from the interior of the base part 1, through the openings 2a, 2b owing to pressure being exerted on the pushbutton 4a.

The device according to the invention is used in the following way: the pushbutton 4a is pushed in against the effect of the spring 5, the loop 6 being ejected through the openings 2a, 2b. The loop 6 is passed over a tick which is to be removed and the pushbutton 4a is released so that the loop 6 is gradually drawn into the interior 3 of the base part 1. Owing to the effect of the spring 5, the tick is thus held fast by the loop 6 without being injured. The device and the loop are now rotated one turn clockwise or anticlockwise and within approximately three seconds the tick releases its grip and can be rendered harmless when it has been removed from the loop 6.

I claim:

1. A device for removing ticks from humans and animals, comprising:

a base part having a tapered tip portion and an opposite back portion, the tip portion having two openings defined therein;

a rod member slidably disposed within the base part, the rod member being movable between an operative position and a retracted position;

a spring having a biasing force, the spring being in operative engagement with the rod member to urge the rod member to the retracted position;

a resilient thread having both ends attached to the rod member so that a loop portion of the resilient thread protrudes out through the two openings at the tip portion of the base part, the loop portion having a size that is reducible as the rod member is moved from the operative position to the retracted position by the spring; and an actuator in operative engagement with the rod member at the back portion of the base part to enlarge the size of the loop portion against the biasing force of the spring.

2. The device according to claim 1 wherein the resilient thread is made of a polymer.

3. A method of removing a tick from humans and animals with the device of claim 1, the method comprises the steps of:

actuating the actuator against the biasing force of the spring to enlarge the size of the loop portion;

placing the resilient thread around the tick;

releasing the actuator to permit the biasing force of the spring to retract the rod member to reduce the size of the loop portion; and turning the base part with the resilient thread placed around the tick.

* * * * *